US00PP09563P

United States Patent [19]

Conklin

[11] Patent Number: Plant 9,563

[45] Date of Patent: May 28, 1996

[54] HYBRID TEA ROSE PLANT 'CONMON'

[76] Inventor: Henry C. Conklin, 13001 W. Solano Dr., Glendale, Ariz. 85340

[21] Appl. No.: 511,880

[22] Filed: Aug. 7, 1995

[51] Int. Cl.[6] ..... A01H 5/00

[52] U.S. Cl. ..... Plt./11

[58] Field of Search ..... Plt./11, 22, 1

[56] References Cited

U.S. PATENT DOCUMENTS

P.P. 4,857 6/1982 Bailey ..... Plt./22

P.P. 6,492 12/1988 Weddle ..... Plt./11

*Primary Examiner*—Howard J. Locker

[57] ABSTRACT

A new and distinct variety of rose plant of the hybrid tea rose class characterized by its upright habit of growth and unusual flower color.

1 Drawing Sheet

BACKGROUND OF THE NEW PLANT

The present invention relates to a new and distinct variety of rose plant of the Hybrid Tea rose class named "CONMON," which was originated by my crossing as seed parent the rose known as "Blue Heaven" (U.S. Plant Pat. No. 3,818) X "Blue Boy" (U.S. Plant Pat. No. 4,857) as pollen parent.

Among the novel characteristics possessed by this new variety which distinguishes it from all other varieties of which I am aware are:

1. Vigorous spreading upright habit of growth;
2. Attractive unique flower color (Red Purple Group 64);
3. Unusual flower form resembling that of an Old Fashioned Garden Rose with continuous blooming habit;
4. Disease resistance and winter hardiness.

Asexual reproduction by budding of the new variety as performed in McFarland, Calif. and Litchfield, Ariz., shows that the foregoing and other distinguishing characteristics come true to form and are established and transmitted through succeeding propagation.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (R.H.S.C.C.). The terminology used in color description herein refers to plate numbers in the aforementioned color chart, e.g., "64-B" is plate 64-B of The Royal Horticultural Society Color Chart.

DESCRIPTION OF THE NEW VARIETY

Flower

A. Bud:
- (1) *Size.*—Medium.
- (2) *Form.*—Cupped.
- (3) *Color.*—When sepals divide bud color is 64-B.
- (4) *Sepals.*—Slightly longer than bud, sparsely foliated.
- (5) *Peduncle.*—Erect, light green/gray color.

B. Bloom:
- (1) *Size.*—Medium 10–11½ cm.

- (2) *Borne.*—Mostly erect.
- (3) *Form.*—Ovoid to cupped.
- (4) *Petalage.*—Heavy number of petals under normal conditions (42).
- (5) *Color.*—64-B (Basic Color).
- (6) *Color change.*—Blends to 64-C to 73-A.

C. Petals:
- (1) *Texture.*—Average.
- (2) *Appearance.*—Inside velvety, outside satiny.
- (3) *Form.*—Rounded and ruffled.
- (4) *Arrangement.*—Imbricated, regularly and slightly cupped.
- (5) *Petaloids in center.*—Few.
- (6) *Persistence.*—Long-lasting, but drop off cleanly.
- (7) *Fragrance.*—Very fragrant.
- (8) *Lasting quality.*—12–14 days.

Reproductive Organs

A. Stamens: Regularly arranged around the pistils.
- (1) *Anthers.*—Color near 17-C.
- (2) *Pollen.*—Color near 17-B.

B. Pistils:
- (1) *Styles.*—Color near 14-B.
- (2) *Stigmas.*—Color near 145-C.

C. Hips: None observed.

Plant

A. Form: Upright vase-shape.

B. Growth: Very vigorous; large; uniform branching on main stems; new growth occurs regularly throughout season from base of plant. Height obtained 126 cm.

C. Blooming habit: Continuous.

D. Foliage: Compound 3–5 leaflets on single bloom; 5–7 leaflets on main canes.
- (1) *Size.*—Medium to large.
- (2) *Quantity.*—Abundant; covers plant to ground.
- (3) *Color.*—a) New Foliage: 1) upperside — near to 183-A with deep green veining. 2) underside — greenish red with 183-C overcast. b) Old Foliage: 1) upperside — holly green; somewhat near, but darker, than 137-B. 2) underside — 147-C.
- (4) *Shape.*—Oval and pointed.
- (5) *Texture.*—a) Upper side — leathery, glossy. b) Under side — smooth between ribs.
- (6) *Edge.*—Serrated.

(7) *Serration.*—Small.
(8) *Leaf stem.*—Color 137-B underside 137-C.
(9) *Stipules.*—Medium smooth.

E. Wood:
(1) *New wood.*—a) Color — 137-C. b) Bark — smooth.
(2) *Old wood.*—a) Color — 137-B. b) Bark — smooth.

F. Thorns:
(1) *Quantity.*—Ordinary on laterals from stalk.
(2) *Form.*—Flat base.
(3) *Length.*—Small.
(4) *Color.*—148-C.
(5) *Position.*—Irregular.

G. Prickles:
(1) *Quantity.*—Few.

H. Disease resistance:
(1) *Mildew.*—Good.
(2) *Blackspot.*—Good.
(3) *Rust.*—Good.

I. Winter hardiness: Good.

I claim:

1. A new and distinct variety of rose plant of the Hybrid Tea class, substantially as shown and described.

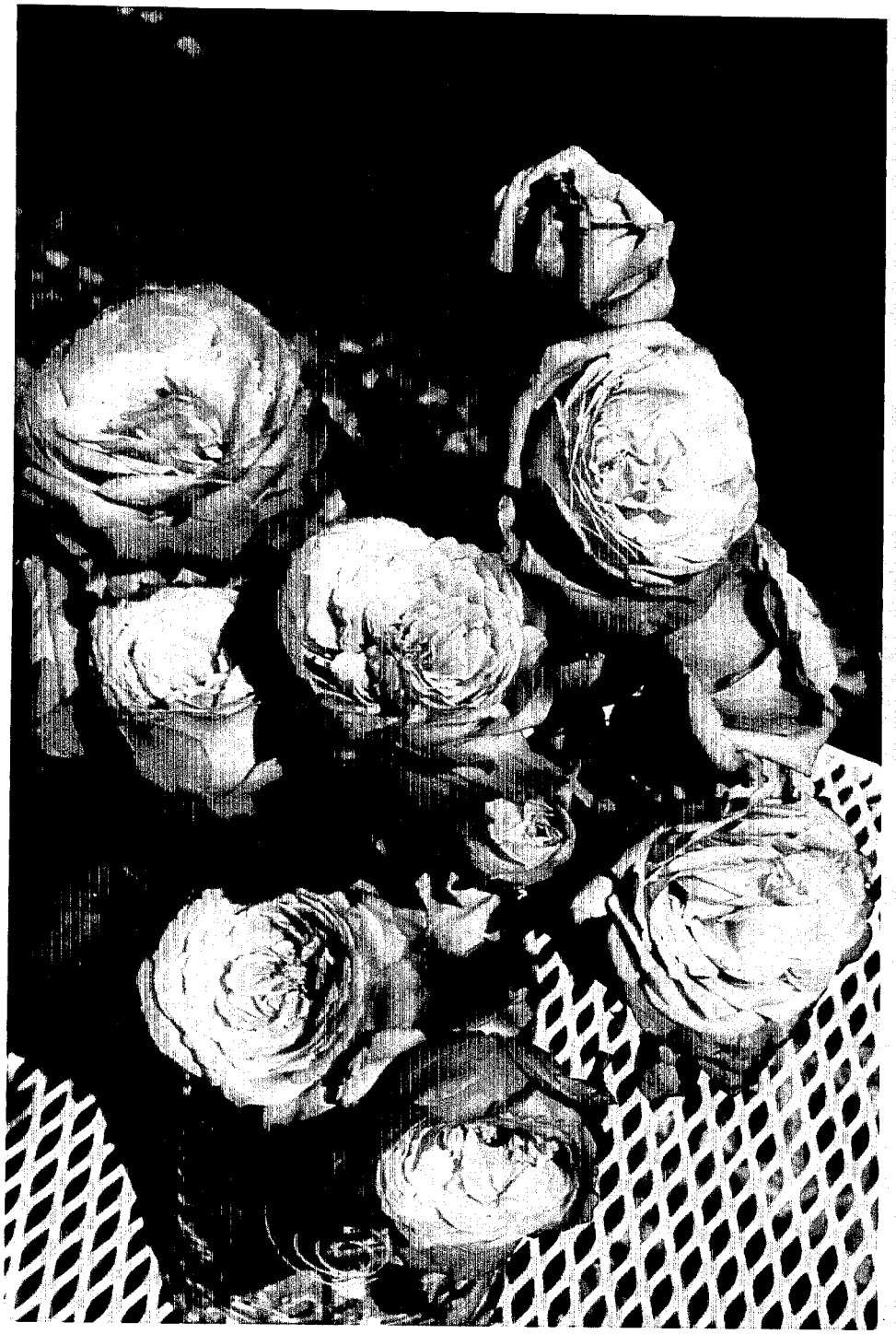

* * * * *